| United States Patent [19] | [11] Patent Number: 4,795,855 |
| Fillatti et al. | [45] Date of Patent: Jan. 3, 1989 |

[54] TRANSFORMATION AND FOREIGN GENE EXPRESSION WITH WOODY SPECIES

[76] Inventors: Joanne Fillatti, 1225 Aspen Pl.; Luca Comai, 1892 Sharon Ave., both of Davis, Calif. 95616

[21] Appl. No.: 832,928

[22] Filed: Feb. 24, 1986

Related U.S. Application Data

[63] Continuation-in-part of Ser. No. 798,050, Nov. 14, 1985, abandoned.

[51] Int. Cl.[4] ............... A01H 1/04; C12N 15/00; C12N 5/00; C12P 21/00
[52] U.S. Cl. ............................... 800/1; 435/68; 435/172.3; 435/240.49; 435/240.54; 935/56; 935/67
[58] Field of Search ............ 435/68, 172.3, 240, 435/241, 240.4, 240.49, 240.54; 800/1

[56] References Cited

U.S. PATENT DOCUMENTS

| 4,459,355 | 7/1984 | Cello et al. | 435/172.3 |
| 4,535,060 | 8/1985 | Comai | 435/172.3 |
| 4,658,082 | 4/1987 | Simpson et al. | 435/172.3 |

OTHER PUBLICATIONS

Rogers et al., 1983, Appl. Div. Microbiol. 46(1): pp. 37–43.
Murai et al., 1983, Science 222: pp. 476–482.
Fraley et al., 1983, Proc. Natl. Acad. Sci. 80: pp. 4803–4807.
Wolter, K. E., 1968, Nature 219: pp. 509–510.
Hock et al., 1971, Phytopathol. 61(2): p. 129.
Goodman et al., 1987, Science, 236: pp. 48–54.
Harsch et al., 1985. Science 228: pp. 1229–1231.

*Primary Examiner*—Charles F. Warren
*Assistant Examiner*—David Fox

[57] ABSTRACT

Woody species, particularly poplar, are produced by transformation of shoot cultures with the foreign DNA and regeneration of plants from transformed cells, where the plants are capable of expression of the foreign gene. Particularly, poplar shoot cultures are employed and are transformed employing a manipulated Agrobacterium transformation system, followed by regeneration of the plant tissue into plants.

12 Claims, No Drawings

TRANSFORMATION AND FOREIGN GENE EXPRESSION WITH WOODY SPECIES

CROSS-REFERENCE TO RELATED APPLICATIONS

This application is a continuation-in-part of application Ser. No. 798,050, filed Nov. 14, 1985, now abandoned, which disclosure is incorporated herein by reference.

BACKGROUND OF THE INVENTION

1. Field of the Invention

There is substantial interest in improving the phenotypes of trees. There are a large number of commercially important timber species, such as the American timber species, redwood (*Sequoia sempervirens*), Loblolly pine (*Pinus taeda*), white spruce (*Picea glauca*), longleaf pine (*Pinus palustris*), western hemlock (*Tsuga heterophylla*) and Douglas fir (*Pseudotsuga mengiesii*), as well as others (Cheng, *Plant and Cell Physiol.* (1976) 17:1347–1350). The potential for modifying trees to make woody species resistant to stress, to accelerate growth, to improve wood or wood pulp qualities is of commercial importance.

Conventional plant breeding methods for trees have been very limited due to the prohibitively long reproduction cycles and high levels of heterozygosity. Therefore, the possibility of employing genetic engineering with woody species appears as an attractive alternative. However, plant cells (including woody species cells) are substantially different from other types of cells in their requirements for a transforming system. First, unlike unicellular microorganisms, the plant cells have a low rate of proliferation. Second, the plant cells are much more sensitive to their environment in relation to viability, proliferation and regeneration to plants. Third, in order to establish whether the foreign gene has been usefully integrated into the plant cell, it is necessary to establish that the regenerated plant expresses the phenotype. Finally, the plant cell has a strong rigid cell wall.

Because of the long time intervals involved between the manipulation of the plant cells and the demonstration of effective expression of the gene, it is essential that at each stage high efficiencies be achieved in transformation, cell growth, and regeneration. Furthermore, there are the additional considerations involved with matching a particular technique and the materials employed in that technique with the particular plant species. In addition, there is the further consideration of the subsequent handling of the transformed culture in order to obtain plants, namely plant regeneration from cells and callus.

BRIEF DESCRIPTION OF THE RELEVANT LITERATURE

McCown, *TAPPI J.* (1985) 68:116–119, describes the use of shoot cultures as clonal propagation systems. The use of *A. tumefaciens* for transforming plants employing leaf disks is described in Horsch et al., *Science* (1985) 228:1229–1231. See also, Herrera-Estrella et al., *Nature* (1983) 303:209–213; Fraley et al., *Proc. Natl. Acad. Sci. USA* (1983) 80:4803–4807; and Bevan et al., *Nature* (1983) 304:184–187. The glyphosate resistant aroA gene is described in Stalker et al., *J. Biol. Chem.* (1985) 260:4724–4728, while transcriptional initiation and termination regions are described by deGreve, *J. Mol. Appl. Genet.* (1983) 1:499–511; Salomon et al., *EMBO J.* (1984) 3:141–146; Velten et al., ibid. (1984) 3:2723–2730; Garfinkel et al., *Cell* (1983) 27:143–153; and Barker et al., *Plant Mol. Bio.* (1983) 2:335–350. Comai et al., *Nature* (1985) 317:741–744, describe the expression of a mutant aroA gene from *Salmonella typhimurium* in plants providing tolerance glyphosate.

SUMMARY OF THE INVENTION

Novel transformed woody species are provided containing novel nucleotide constructions capable of stable expression in the woody species. High efficiency transforming techniques are employed which result in a high proportion of normal transformed cells, which are then efficiently regenerated to plants. The technique provides for stable expression of foreign genes, particularly genes providing novel phenotypes for the plants.

DESCRIPTION OF THE SPECIFIC EMBODIMENTS

Novel procedures and products are provided involving the introduction of novel nucleotide constructs into cells of woody species and regeneration of the transformed cells, where the transformed cells in the plants express one or more genes present in the construct, so as to provide at least one novel property for the plant, particularly a phenotypic property. The woody species which can be transformed are trees, particularly those trees employed for commercial purposes and subject to forest management, both conifer and deciduous. Such trees include poplar, eucalyptus, Douglas fir, pine, e.g., Loblolly, sugar and Monterey, nut trees, e.g., walnut and almond, fruit trees, e.g., apple, plum, citrus and apricot, hardwood trees, such as ash, birch, oak, and teak, etc. The subject methodology has been demonstrated for poplar.

In referring to woody species is intended vegetation which is characterized by being dicotyledenous, perennial, accumulates wood core and normally finds use as a source for wood pulp or lumber. Other species not normally considered trees which share many of these characteristics are such plants as rhododendrons and roses.

The transformed plant cells may be cells in culture, may be present as a disorganized mass in callus, as leaf explants, shoot cultures, seeds, trees, leaves, roots, or the like. The foreign construct will normally be present in all or substantially all of the cells of the tree tissue, but expression may be limited to particular cells or particular times in the development of the tree. The foreign construct will include transcriptional and translational initiation and termination signals, with the initiation signals 5' to the gene of interest and the termination signals 3' to the gene of interest.

The transcriptional initiation region which includes the RNA polymerase binding site (promoter) may be native to the woody host or may be derived from an alternative source, where the region is functional in the woody host. Other sources include the Agrobacterium T-DNA genes, such as the transcriptional initiation regions for the biosynthesis of nopaline, octopine, mannopine, or other opine transcriptional initiation region, transcriptional initiation regions from plants or other woody species than the host species, transcriptional initiation regions from viruses, particularly host specific viruses, or partially or wholly synthetic transcription initiation regions.

The transcriptional initiation regions may not only include the RNA polymerase binding site, but also regions providing for regulation of the transcription, where the regulation involves chemical or physical repression or induction, e.g., metabolites or light, regulation based on cell differentiation, such as associated with leaves, roots, seed, or the like. Thus, the transcriptional initiation region or the regulatory portion of such region is obtained from an appropriate gene, which is regulated, for example, the 1,5-ribulose biphosphate carboxylase gene, which is light-induced, and used for transcriptional initiation, stress-induced genes, heat shock genes, which are temperature regulated, wound induced genes, meristem specific genes, etc.

The 3' termination region may be derived from the same gene as the transcriptional initiation region or a different gene. For example, where the gene of interest has a transcriptional termination region functional in the woody species, that region may be retained with the gene.

An expression cassette can be constructed which will include the transcriptional initiation region, the gene of interest under the transcriptional regulational control of the transcriptional initiation region, the initiation codon, the coding sequence of the gene, with or without introns, the translational stop codons, followed by the transcriptional termination region, which will include the terminator, and may include a polyadenylation signal sequence, and other sequences associated with transcriptional termination. The direction is 5'-3' in the direction of transcription. The cassette will usually be less than about 10 kb, frequently less than about 6 kb, usually being at least about 1 kb, more usually being at least about 2 kb.

The gene of interest may be derived from a chromosomal gene, cDNA, a synthetic gene, or combinations thereof. Where the expression product of the gene is to be located in other than the cytoplasm, the gene will usually be constructed to include particular amino acid sequences which result in translocation of the product to a particular site, which may be an organelle, such as the chloroplast, mitochondrion or nucleus, the cell plasma membrane, or may be secreted into the periplasmic space or into the external environment of the cell. Various secretory leaders, membrane integrator sequences, and translocation sequences for directing the peptide expression product to a particular site are described in the literature. See, for example, Cashmore et al., *Biotechnology* (1985) 3:803-808, Wickner and Lodish, *Science* (1985) 230:400-407.

Genes of interest for use in woody species include a wide variety of phenotypic and non-phenotypic properties. Among the phenotypic properties are enzymes which provide for resistance to stress, such as dehydration resulting from heat and salinity, herbicides, toxic metal or trace elements, or the like. Resistance may be as a result of a change in the target site, enhancement of the amount of the target protein in the host cell, the increase in one or more enzymes involved with the biosynthetic pathway to a product which protects the host against the stress, and the like. Genes may be obtained from prokaryotes or eukaryotes, bacteria, fungi, e.g., yeast, viruses, plants, mammals or be synthesized in whole or in part. Illustrative genes include glyphosate resistant 3-enolpyruvylphosphoshikimate synthase gene, nitrilase, genes in the proline and glutamine biosynthetic pathway, metallothioneins, etc. Other genes of interest may be involved with regulation of growth, such as manipulations of source/sink (carbon partitioning) relations, e.g., changes in solids content, or apical dominance, photosynthetic efficiency, such as altering the efficiency of RuBP carboxylase, or changing the quality of the woods, such as altering lignin to cellulose ratios or the length of wood fibers.

One or more cassettes may be involved, where the cassettes may be employed in tandem for the expression of independent genes which may express products independently of each other or may be regulated concurrently, where the products may act independently or in conjunction.

Where the expression cassette is to be transformed into plant cells by means of Agrobacterium, the cassette will be bordered usually within at least about 1 kb by the right and/or left T-DNA borders. These borders may be obtained from any Ti- or Ri-plasmid and may be joined to the expression cassette by conventional ways. The expression cassette may be constructed so as to be directly transferred from a plasmid other than a Ti- or Ri-plasmid or may become integrated into the T-DNA region of a Ti- or Ri-plasmid through homologous recombination. Thus, the expression cassette could have DNA sequences at one or both borders of the expression cassette homologous with sequences present in the T-DNA region of the Ti- or Ri-plasmid.

The expression cassette will normally be carried on a vector having at least one replication system. For convenience, it is common to have a replication system functional in *E. coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. These plasmids are particularly effective with Ti-plasmids, either armed or disarmed, for transfer of T-DNA to the woody species host.

In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the woody species host. The markers may be protection against a biocide, such as antibiotics, toxins, heavy metals, or the like; or complementation, imparting prototrophy to an auxotrophic host. Various genes which may be employed include neomycin phosphotransferase (NPTII), hygromycin phosphotransferase (HPT), chloramphenicol aminotransferase (CAT), nitrilase, gentamicin resistance gene, etc. For plant host selection, markers of particular interest include NPTII, providing kanamycin resistance or G418 resistance, HPT, providing hygromycin resistance, CAT, providing chloramphenicol resistance, mutated aroA gene providing glyphosate resistance, etc.

The various fragments comprising the various constructs, expression cassettes, markers, and the like may be introduced consecutively by restriction enzyme cleavage of an appropriate replication system, and insertion of the particular construct or fragment into the available site. After ligation and cloning the vector may be isolated for further manipulation. All of these techniques are amply exemplified in the literature and find particular exemplification in Maniatis et al., *Moleular*

*Cloning: A Laboratory Manual,* Cold Spring Harbor Laboratory, Cold Spring Harbor, N.Y., 1982.

Once the vector is completed, the vector may now be introduced into plant cells. Techniques for transforming plant cells include microinjection, direct DNA uptake using polyethylene glycol, electroporation, viral infection, and transformation with Agrobacterium. In accordance with the subject invention, an efficient method has been developed for transformation of woody species employing Agrobacterium. This technique provides a methodology for the transformation of woody species with foreign genes in an efficient manner, so as to provide a rapid technique for transforming plant cells and regeneration of plants in an efficient reproducible manner.

Sterile shoot cultures are employed as a source for poplar leaves. The leaves are cut into sections of about 0.5 to 3 $cm^2$ surface area and placed on feeder plates for an extended period of time, usually at least 12 hr and not more than about 48 hr. The cells of the feeder plates act as a nurse culture for the poplar leaves as well as enhancing the efficiency of the transformation rate. Any convenient cell suspension may be employed, such as tobacco or corn, particularly the former.

The feeder plates are prepared by employing a plant suspension culture, e.g., Nicotiana cells, in a soft agar medium, generally having from about 0.5 to 1% agar and containing an appropriate growth medium, such as Murashige and Skoog salts, a carbon source, e.g., sucrose, and appropriate amounts of hormones, auxins, such as 2,4-dichlorophenoxyacetic acid (2,4-D), kinetin and vitimins, such as thiamine, with a medium appropriately buffered in the range from 5 to 6, preferably 5.5. The kinetin and thiamine will generally be about 0.75 to 1.5 mg/L, while the 2,4-D will generally be about 0.05 to 0.2 mg/L. Desirably, the feeder plates are prepared prior to being used, conveniently at least two days prior to being used.

The feeder plates are covered to prevent the feeder cells from coming into contact with the leaf explants. This can be readily achieved employing a sterile filter paper disk. The leaves are then allowed to preincubate, followed by transfer to a broth culture of the Agrobacterium strain containing the construction for integration and the genetic capability for transfer of the construct into the plant cells. Generally, the number of bacteria will be from about $10^8$ to $10^{10}$/ml. The contact with the bacteria in the bacterial broth culture, e.g., MG/L (same as LBMG; see Garfinkel et al., *J. Bacteriol.* (1980) 144:732–743), will usually be at least about 15 min and not more than about 60 min, usually averaging about 30 min. The leaf sections are then transferred from the bacterial broth, excess surface liquid removed and the leaf sections returned to the feeder plates. Cocultivation of the leaf sections with the bacteria is continued for from about 8 hr to 2 weeks, ususally about 72 to 96 hr, before transferring the leaf sections to a regeneration medium.

The regeneration medium will contain a bacteriocide, e.g., carbenicillin and a selective reagent for selecting transformed cells. For example, with the kanamycin resistance gene (NPTII), kanamycin will be added to at least about 30 mg/L and usually not more than about 100 mg/L, preferably from about 50 to 80 mg/L in the selective medium. The regeneration medium will include an appropriate carbon source, such as Murashige minimal organics medium, with appropriate hormones at individual levels of about 0.75–1.25 mg/L, such as 6-benzylaminopurine at about 1 mg/L and zeatin at about 1 mg/L. Conveniently, the regeneration medium is a soft agar, containing about 0.5 to 1.0% agar, with the regeneration being buffered in the same range described previously.

In 2 to 3 weeks morphogenic callus and shoots will be observed. When shoots are approximately 1 to 2 cm, they may be excised and transferred to Murashige and Skoog media to root.

The Agrobacterium system which is employed involves the use of a wild-type strain, particularly *A. tumefaciens* C58. (Larcheke et al., *Nature* (1974) 252:169–70; Matzke and Chilton, *J. Mol. Appl. Gen.* (1981) 1:39–49; Zambryski et al., *EMBO J.* (1983) 2:2143–2150) Agrobacterium C58 is characterized by the following characteristics: biotype 1, nopaline production from tumors, 3-ketolactose positive. The Agrobacterium to be employed as the transformation system will be transformed itself with a wide host range plasmid that can shuttle DNA from *E. coli* into Agrobacterium. This is achieved by having a P-1 incompatibility plasmid replicon, e.g., RK2, and plasmid replicon capable of providing multicopies in *E. coli*, usually at least 5, preferably at least 10, and up to 200 copies in *E. coli*. The wide host range plasmid will be characterized by having at least one T-DNA border sequence, particularly the right border sequence, or conveniently having both border sequences separated in one direction by the various constructs intended to be integrated into the woody species genome. The Agrobacterium strain may have either a disarmed Ti- or Ri-plasmid or an armed Ti- or Ri-plasmid, preferably armed. By disarmed is intended the absence of the sufficient T-DNA to result in homologous recombination with the T-DNA present on the wide host range plasmid, while the Ti- or Ri-plasmid still retains the vir genes to effect transfer and integration of the T-DNA construct into the plant cells.

With an arme plasmid, high rates of shoot regeneration are obtained, thus, an increased proportion of transformed cells develop into shoots. A fraction of these transformed shoots have a normal phenotype, develop roots and do not produce opines, while other shoots are abnormal, produce opines and lack the ability to root. It appears that the production of phytohormones by the wild type-DNA stimulates high rates of regeneration from poplar leaf explants. In the absence of endogenous phytohormone sources, rates of explant regeneration are low, so that the regeneration of plants from the cells subjected to cocultivation transformation is very low. Using armed binary vectors at least about 60% regeneration is achieved, with rates of regeneration up to 85% or higher. With the disarmed binary vector regeneration is as low as 0%.

Plants may then be grown and selected for resistance to a biocide, expression of the desired gene(s) and be monitored by Northern and Western blots, immunoassays, and the like.

Of particular interest are woody species which are resistant to one or more herbicides, so that the woody species can be grown in an environment where there is no competition for nutrients and trace metals by weeds. In this way, woody species can be grown efficiently and economically, where nutrients supplied to the woody species will be primarily metabolized by the woody species.

The following examples are offered by way of illustration and not by way of limitation.

EXPERIMENTAL

*E. coli* strain MM294 (Hanahan, *J. Mol. Biol.* (1983) 116:557–580) was used as the host for binary vectors containing the pRK290 type replicon. Agrobacterium strain C58 has been described supra. RC2760 is another designation for Agrobacterium strain LBA4404 (Hoekema et al., *Nature* (1983) 303:179–180). Strain K12 was generated by transforming pTiA6 into strain A114 (NT1) (Nester and Kosuge, *Ann. Rev. Microbiol.*, (1981) 35:531, Hoekema et al., *Nature* (1983) 303:179). Levels of antibiotics used with *E. coli* in mg/l were 30 for kanamycin, 50 for chloramphenicol, 300 for penicillin, 10 for tetracycline and 20 for gentamicin. Unless otherwise indicated, levels of antibiotics used with Agrobacterium in mg/l were 100 for kanamycin or gentamicin and 50 for carbenicillin or chloramphenicol.

Laboratory Procedures

Restriction enzymes and T4 ligase were obtained from commercial sources and used according to manufacturers' recommendations. Standard methods of cloning and molecular analysis were performed as described in Maniatis et al., supra.

Constructions

The BglII-SmaI fragment of Tn5 containing the entire structural gene for APHII (Jorgensen et al., *Mol. Gen.* (1979) 177:65) was cloned into pUC8 (Vieira and Messing, *Gene* (1982) 19:259), converting the fragment into a HindIII-EcoRI fragment, since there is an EcoRI site immediately adjacent to the SmaI site. The PstI-EcoRI fragment containing the 3' portion of the APHII gene was then combined with an EcoRI -BamHI-SalI-PstI linker into the EcoRI site of pUC7 (pCGN546W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a Sau3A-PstI fragment from the 5'-end of APHII, which fragment lacks the superfluous ATG, into the BamHI-PstI site of pCGN546W to provide plasmid pCGN550.

The EcoRI fragment containing the APHII gene (1ATG) was then cloned into the unique EcoRI site of pCGN451, which contains an octopine synthase cassette for expression to provide pCGN552(1ATG).

pCGN451 includes an octopine cassette which contains about 1556 bp of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows. A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-transcribed region, the mRNA cap site and 16 bp of the 5' non-translated region (to a BamHI site) intact. This small fragment was obtained by size fractionation on a 7% acrylamide gel and fragments approximately 130 bp long eluted. This size fractionated DNA was ligated into M13mp9 and several clones sequenced and the sequence compared to the known sequence of the octopine synthase gene. The M13 construct was designated pI4, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences. The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5' non-translated sequence) and the 3' region (which contains 267 bp of the coding region, the stop codon, 196 bp of 3' non-translated DNA, the polyA site and 1,153 bp of 3' non-transcribed sequence).

The resulting plasmid pCGN451 having the ocs 5' and the ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation.

This ocs/KAN gene was used to provide a selectable marker for the trans type binary vector pCGN587.

The 5' portion of the engineered octopine synthase promoter cassette consists of TiA6 DNA from the XhoI fragment at bp 15208–13644 (Barker's numbering), which also contains the T-DNA boundary sequence (border) implicated in T-DNA transfer. In the plasmid pCGN587, the ocs/KAN gene from pCGN552 provides a selectable marker as well as the right border. The left boundary region was recloned from the HindIII-EcoI fragment as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglII fragment of pVCK102 (Knauf and Nester, *Plasmid* (1982) 8:45), creating pCGN585.

Construction of pPMG85

To construct pPMG85, the mannopine synthase gene (mas) 5' region from pTiA6 (Salomon et al., *EMBO J.* (1984) 3:141–146). The gene was obtained from a cosmid clone carrying the T-DNAs of pTiA6 called pVCK232 (Knauf and Nester, *Plasmid* (1982) 8:45–54). pVCK232 was digested with EcoRI and one of the resulting fragments called Eco13 or EcoC was cloned in pACYC184 to provide plasmid pCGN14. Digestion of pCGN14 with ClaI and SphI yielded a mixture of fragments with the desired fragment resulting from cleavage at the ClaI site 20128 to the SphI site 21562 (Barker et al., *Plant Mol. Bio.* (1983) 2:335–350). This fragment contains the mas 5' region and was cloned in pUC19 (Yanisch-Perron et al., Gene (1985) 3:103-119) which had been linearized with SphI and AccI to provide plasmid pCGN40. The aroA BamHI fragment from pPMG34 (Stalker et al., *J. Biol. Chem.* (1985) 260:4724-4728) was cloned in the proper orientation in pCGN40, where the aroA gene was fused to the mas promoter region, providing pPMG67.

To provide a polyadenylation signal, the tml 3' region of pTiA6 (Garfinkel et al., Cell (1983) 27:143-153) was used. A T-DNA BamHI fragment (9062-13774; Barker numbering) containing such region was cloned from pVCK232 in pACYC184 in the orientation where nucleotide 13774 was proximal to the HindIII site of the vector. The resulting plasmid was digested with SmaI, which cleaves at nucleotide 11210 (Barker numbering) of the tml 3' region and an octomeric XhoI linker (New England Biolabs) inserted. The resulting plasmid pBamX was digested with HindIII and XhoI and a fragment containing most of the mas 5' region and the aroA gene obtained by digestion of pPMG67 with HindIII and SalI cloned into the linearized pBamX. The resulting plasmid pPMG73 contained 5'-mas-aroA-tml-3' hybrid gene.

To allow for efficient selection in Agrobacterium, the kanamycin resistance gene from pUC4K (Vieira and Messing, *Gene* (1982) 19:259-268) was excised from SalI and cloned in a XhoI site present in the aroA distal end of the mas 5' region giving pPMG76.

A 2.0 kb EcoRI fragment in the Hind17 region of pRiA4T-LT-DNA (White and Nester, *J. Bacteriol.* (1980) 141:1134; Taylor et al., *Mol. Gen. Genet.* (1985) 201:546) was cloned in the chloramphenicol resistance gene EcoRI site of pPMG76 yielding pPMG82.

To allow selection of transformed plants on kanamycin, a mas-npt hybrid gene was constructed. (See Velten et al., *EMBO J.* (1984) 3:2723-2730 for an analogous construction.) The mas 5' region was excised from pCGN40 by digestion with EcoRV (21552; Barker numbering) and EcoRI (in the pUC19 polylinker) and cloned in pCGN451 digested with SmaI and EcoRI. The restriction deletes all of the ocs 5' region from pCGN451 and inserts the mas 5' region in its place. In addition, part of the pUC19 polylinker from XbaI to EcoRI is placed between the mas promoter region and the ocs polyadenylation site, allowing a choice of different sites for insertion of genes to be expressed. In the EcoRI site of this plasmid pCGN46, an EcoRI fragment of pCGN552, carrying the Tn5 npt gene (Rothstein et al., *Cell* (1980) 19:795-805), is inserted where an untranslated ATG sequence in the 5' region had been removed.

The hybrid mas-npt-ocs gene was excised by digestion with XhoI and cloned in the SalI site of pPMG82 resulting in pPMG85.

The resulting plasmid pPMG85 contained beginning from the EcoRI site, an EcoRI-HindIII 1.5 kb fragment from pACYC184 and going clockwise, the bacterial kanamycin resistance gene from pUC4K, the mas 5= region nucleotides 21476 to 20128, oriented in the clokkwise direction, a BamHI-SalI aroA containing fragment from pPMG34, the tml 3' region from nucleotides 11207 to 9062, a BamHI-SalI fragment from the tetracycline resistance gene of pACYC184, the npt gene from pCGN552, a 2.5 kb SalI-EcoRI fragment from pACYC184 and a 2 kb EcoRI fragment from pRIA4 on the BglII-HindIII-17 fragment (Huffman et al., *J. Bacteriol.* (1984) 157:269-276).

Transformation of Poplar Cells

Poplar leaves were obtained from sterile shoot cultures which had been grown at 24° C., with a 16 hr/8 hr day/night cycle in magenta boxes containing Murashige-Skoog salt medium and 0.8% agar (pH 6.0). See McCown, supra, which is incorporated herein by reference. The leaves were cut into sections of 2 cm$^2$ and placed onto feeder plates for a 24 hr preincubation. The feeder plates were prepared by pipetting 1 ml of a tobacco suspension culture ($\sim$107-108 cells/ml) onto 0.8% agar medium, containing Murashige minimal organic medium (K.C. Biologicals), 2,4-D (0.1 mg/L), kinetin (1 mg/L), thiamine (0.9 mg/L) and potassium acid phosphate (200 mg/L, pH 5.5). The feeder plates were prepared two days prior to use. A sterile 3 mm filter paper disk was placed on top of the tobacco cells after the suspension cells had grown for two days.

Following the preincubation period, the leaf sections were placed into a liquid MG/L broth culture (5-10ml) of the *Agrobacterium tumefaciens* strain C58/587/85 ($8 \times 10^8$ bacteria/ml). (The plasmids pCGN587 and pPMG85 were transformed into *E. coli* C2110 (polA) and cointegrates selected by kan$^r$ and glyphosate resistance, de Fromard et al, *BioTechnology*, May 1983, pp. 262-267.) After 30 min, the leaf sections were removed from the bacterial broth, lightly blotted and replaced onto the feeder plates. Leaf sections were cocultivated with the bacteria for 72-96 hr and then transferred to regeneration medium containing 500 mg/L carbenicillin and 60 mg/L or 0 mg/L kanamycin. The regeneration medium is a GIBCO Murashige minimal organics medium with 6-benzylaminopurine (1 mg/L) and zeatin (1 mg/L) containing 0.6% agar (pH 5.5). In 2 to 3 weeks, morphogenic callus and shoots were observed to develop. When the shoots were approximately 1.25 cm, they were excised and transferred to a Murashige and Skoog medium for rooting.

Shoots which developed and subsequently rooted on media containing the kanamycin were tested for APH enzyme activity and for the presence of the aroA protein. Extract of poplar leaves showed a positive band for aroA protein in a Western blot (Burnette, *Anal. Biochem.* (1981) 112:195-203). Antibodies employed in the Western blot had been obtained by conventional procedures, immunizing a rabbit with the mutated glyphosate resistant aroA gene expression product. See U.S. Pat. No. 4,535,060, which relevant disclosure is incorporated herein by reference. The presence of the correct band in the gel demonstrates that the glyphosate resistant enzyme is expressed and is stable in the host cell.

An aminoglycoside phosphotransferase enzyme (APH 3'II) assay was conducted on putative transformed poplar plants and shoots. Six of the eight poplar plants tested were positive for APH 3'II enzyme activity. APH 3'II confers resistance to kanamycin and neomycin. APH 3'II activity was assayed (Reiss et al., *Gene* (1984) 30:211-218) employing electrophoretic separation of the enzyme from other interfering proteins and detection of its enzymatic activity by in situ phosphorylation of kanamycin. Both kanamycin and [$\gamma$-$^{32}$P] ATP act as substrates and are embedded in an agarose gel which is placed on top of the polyacrylamide gel containing the proteins. After the enzymatic reaction, the phosphorylated kanamycin is transferred to P-81 phosphocellulose ion exchange paper and the radiolabeled kanamycin is finally visualized by autoradiography.

The Reiss et al. method was modified in the final washing of the P-81 ion exchange.

To further demonstrate the expression of the aroA gene, slot blots were performed substantially according to the procedure of Burnett, *Anal. Biochem.* (1981) 112:195–203. The procedure involves grinding all tissue in liquid nitrogen and then adding extraction buffer (1 μg/1 μl). The extraction buffer is 100 mM sodium citrate (pH 5.6), 0.5 M NaCl, 0.5% SDS, 10 mM EDTA, 1 mM DTT, 10 mM PMSF, 10 mM thiourea and 10 mM leupeptin. After addition of the extraction buffer, grinding is continued, followed by a 5 min spin in the microfuge. The supernatant is removed and spun in an airfuge for 10 min. The supernatant is transferred to a refrigerator until tested.

The testing procedure involved wetting nitrocellulose and blotter paper with 1 mM sodium citrate (pH 5.6), 0.5M NaCl and 0.05% SDS. Samples were loaded onto the nitrocellulose using a Sehleicher and Schuell minifold II Slot Blotter. The nitrocellulose was then washed (Burnett, supra).

The test samples were either leaf or callus tissue which developed on kanamycin containing regeneration media from poplar leaf explants previously co-cultured with *A. tumefaciens* strain C58/587/85. Of the five samples tested, one control leaf sample, two poplar callus samples and two leaf tissue samples, the two callus and one leaf tissue sample demonstrated the stable expression of the aroA gene, while the control and one leaf tissue sample were negative.

The poplar regeneration system described above was found to be rapid and efficient. Over 60% of the co-cultivated explants subsequently developed shoots on kanamycin selective medium. Between 5 to 10 shoots developed per explant. After 6 weeks, 10 to 20 shoots develop per explant.

The above results demonstrate that woody species can be transformed efficiently, whereby foreign genes may be integrated into the plant genome and expressed, providing novel phenotypic properties. Thus, woody species can be transformed and are shown to be capable of utilizing promoters from a variety of other genes, e.g., the T-DNA genes, where the transformed cells may be regenerated into plants which provide for expression of the novel phenotype. By virtue of the high transformation efficiency, successful transformations can be achieved within reasonable time periods and without unduly repetitive procedures. As evidenced by the above disclosure, woody species such as poplar trees are provided which can be protected from herbicides, so that more efficient growth and production of poplar can be achieved.

Although the foregoing invention has been described in some detail by way of illustration and example for purposes of clarity of understanding, it will be obvious that certain changes and modifications may be practiced within the scope of the appended claims.

What is claimed is:

1. A transformed poplar plant comprising transformed cells, said cells comprising a DNA construct as a result of transforming of poplar cells with said DNA construct, which construct comprises in the 5'-3' direction (1) a transcription-initiation region; (2) an open reading frame other than T-DNA expressing a peptide downstream from said transcription-initiation region, and under the transciptional regulation of said transcription-initiation region; and (3) a transcription-termination region to provide an expression cassette capable of expression in said cells, wherein at least one of said open reading frame, transcription initiation region, and transcription termination region is from a plant other than poplar, and wherein said expression cassette is bordered by at least the right T-DNA border, and wherein said construct is a result of joining in vitro at least two of (1), (2), and (3) and said right T-DNA border.

2. A plant according to claim 1, wherein said open reading frame expresses a peptide imparting a phenotypic property to said plant.

3. A plant according to claim 2, wherein said phenotypic property is an enzyme resistant to herbicide.

4. A poplar plant according to claim 1, wherein said plant is a tree.

5. A poplar plant according to claim 4, wherein said peptide is a glyphosphate resistant 3-enolpyruvylphosphoshikimate synthase.

6. A poplar plant according to claim 4, wherein said peptide is an enyzme imparting kanamycin resistance.

7. Stably transformed poplar seedlings comprising cells comprising a DNA construct as a result of transformation of poplar cells with said DNA construct, which construct comprises in the 5'-3' direction: (1) a transcription initiation region, (2) an open reading frame, other than T-DNA, encoding a peptide, said open reading frame downstream from said transcription initiation region and under the transcriptional regulation of said transcription initiation region, and (3) a transcription termination region, to provide an expression cassette capable of expression in said poplar cells, wherein at least one of said open reading frame, transcription initiation region, and transcription termination region is from a plant other than poplar, and wherein said construct is as a result of joining in vitro at least two of (1), (2), and (3).

8. Poplar seedlings according to claim 7, wherein said peptide is an enyzme imparting kanamycin resistance.

9. A method for transforming a poplar plant which comprises:
preincubating poplar leaf explants from shoot cultures with a medium conditioned with plant cells;
cocultivating said leaf explants with *Agrobacterium tumefaciens* comprising an armed Ti-plasmid containing vir genes and an expression construct comprising transcriptional initiation and termination regulatory regions functional in said poplar and a gene other than the wild-type gene of one or both of the initiation and termination regions and under their regulatory control, bordered by at least the right T-DNA border, whereby said expression construct becomes integrated into the genome of cells of said leaf explant;
transferring said leaf explants after cocultivation to a regeneration medium comprising plant hormones and phytohormones produced by a Ti-plasmid comprising *A. tumefaciens* strain, whereby callus is formed and shoots develop; and
transferring shoots to growing medium to produce a poplar plant.

10. A method according to claim 9, wherein said regeneration medium contains at least one of 6-benzylaminopurine or zeatin at a concentration of 0.75 to 1.25 ng/L.

11. A stably transformed poplar plant comprising transformed cells, said cells comprising a DNA construct as a result of transformation of poplar cells with said DNA construct, which construct comprises in the 5'-3' direction (1) a transcription-initiation region; (2) a mutated aroA gene providing glyphosate resistance downstream from said transcription-initiation region and under the transcriptional regulation of said transcription-initiation region; and (3) a transcription-termination region to provide an expression cassette capable of expression in said cells wherein at least one of said gene, transcription initiation region, and transcription termination region is from a plant other than poplar, wherein said construct is a result of joining in vitro at least two of (1), (2), and (3), wherein said poplar plant is transformed according to the method of claim 9.

12. A transformed poplar plant according to claim 11, wherein said plant is a seedling.

* * * * *

UNITED STATES PATENT AND TRADEMARK OFFICE
CERTIFICATE OF CORRECTION

PATENT NO. : 4,795,855

DATED : January 3, 1989

INVENTOR(S) : Fillati et al.

It is certified that error appears in the above-identified patent and that said Letters Patent is hereby corrected as shown below:

ON TITLE PAGE:

[56] Column 2, after line 12, insert --Attorney, Agent or Firm - Bertram I. Rowland, Barbara Rae-Venter.--
Column 6, line 39, replace "arme" with --armed--
Column 9, line 59, replace "mas 5=" with --mas 5'--
Column 10, line 23, replace "polA" with --polA1--
Column 11, line 19, replace "Sehleicher" with --Schleicher--
Claim 1, line 1, after "A", insert --stably--
Claim 1, line 3, replace "transforming" with --transformation--
Claim 5, line 2, replace "glyphosphate" with --glyphosate--

Signed and Sealed this

Tenth Day of September, 1991

*Attest:*

HARRY F. MANBECK, JR.

*Attesting Officer*     *Commissioner of Patents and Trademarks*